United States Patent [19]

Liang

[11] Patent Number: 5,458,906
[45] Date of Patent: Oct. 17, 1995

[54] METHOD OF PRODUCING ANTIBACTERIAL FIBERS

[76] Inventor: Paul M. S. Liang, 9f, 21, Lane 1, Section 4, Cheng-Der Road, Taipei, Taiwan

[21] Appl. No.: 120,068

[22] Filed: Sep. 13, 1993

[51] Int. Cl.⁶ .............................. B05D 1/18; A61K 33/34
[52] U.S. Cl. .................. 427/2.31; 427/343; 427/430.1; 427/443.1
[58] Field of Search .................... 427/2.31, 393.1, 427/443.1, 430.1, 337, 343

[56] References Cited

U.S. PATENT DOCUMENTS

| | | | |
|---|---|---|---|
| 2,791,518 | 5/1957 | Stokes, Jr. et al. | 427/2.31 |
| 3,893,936 | 7/1975 | Hubele | 252/106 |
| 3,961,933 | 6/1976 | Kuyama et al. | 71/67 |
| 4,075,326 | 2/1978 | Kuyama et al. | 424/630 |
| 4,122,143 | 10/1978 | Momotari et al. | 264/104 |
| 4,267,233 | 5/1981 | Tanaka et al. | 428/389 |
| 4,279,960 | 7/1981 | Smeltz et al. | 427/393.1 |
| 4,336,028 | 6/1982 | Tomibe et al. | 8/624 |
| 4,410,593 | 10/1983 | Tomibe et al. | 428/389 |
| 4,692,225 | 9/1987 | Witucki et al. | 427/222 |
| 4,743,476 | 5/1988 | Miller | 427/393.1 |
| 4,755,394 | 7/1988 | Aoki et al. | 427/123 |
| 4,861,663 | 8/1989 | Sirinyan et al. | 427/393.1 |
| 5,108,829 | 4/1992 | Kuhn | 427/389.9 |
| 5,190,788 | 3/1993 | Liang et al. | 427/2 |
| 5,405,644 | 4/1995 | Ohsumi et al. | 427/2.31 |

OTHER PUBLICATIONS

Poly (Metal Acrylate) Finishes for Antibacterial Cotton, S. P. Rowland, Amer. Dyestuff Reporter, Jul. 1976, pp. 46–47.
Antibacterial Finishes, D. D. Gagliardi, American Dyestuff Reporter, Jan. 1962, pp. 31–40.
Application and evaluation of anti–microbial finishes, Peter J. Radford, Amer. Dyestuff Reporter, Nov. 1973, pp. 48–59.
The Role of Bacteria in the Development of Perspiration Odor on Fabrics, Amer. Dyestuff Reporter, Dec. 1963, pp. 87–90.

*Primary Examiner*—Diana Dudash
*Attorney, Agent, or Firm*—Grace J. Fishel

[57] ABSTRACT

Antibacterial fibers are disclosed which are produced by immersing fibers in a solution containing a copper compound, as monovalent copper cations, and at the same time or subsequently treating the fibers in a solution containing carbonate and/or borate anions.

8 Claims, No Drawings

METHOD OF PRODUCING ANTIBACTERIAL FIBERS

BACKGROUND OF THE INVENTION

1. Field of the Invention

The present invention relates to antibacterial fibers and a method for producing antibacterial fibers.

2. Brief Description of the Prior Art

Controlling bacterial growth in fabrics and in particular controlling perspiration odor in clothing, bed cloths and so forth is of continuing interest. There are a number of antibacterial fibers on the market, all of which have shortcomings. For example, the Japanese company Toyobo treats fibers with DC 5700, a silicone quaternary ammonium salt sold by Dow Corning. Fabrics made with Toyobo fibers lose antibacterial power during washing. The Japanese company Nihonsambo uses Cus-Silperlon but the treated fibers displays a green color and are very difficult to dye. The Japanese company Iiasi uses ceramic products called Zeomic to remove odors by absorption, less effectively than antibacterial chemicals which can limit odor formation. Various spray-on coatings of antibacterial chemicals have been used but the fibers suffer worse fastness and poor antibacterial power. Other treatment systems include U.S. Pat. No. 5,190,788 which teaches the use of cuprous iodide for producing a fabric with antibacterial properties. The photosensitive properties of cuprous iodide, however, can result in a yellowing of the treated fabric which may limit the use of the fabric in certain applications.

SUMMARY OF THE INVENTION

In view of the above, it is an object of the present invention to provide a method of treating fibers to give the fibers antibacterial properties with chemicals which are not photosensitive. It is another object to provide treated fibers which can be dyed by conventional means and which retain good mechanical properties. It is a further object to provide treated fibers with antibacterial properties for use in various spun, woven knitted and non-woven fiber masses, which antibacterial properties are sustained during washing. This combination of features is highly desirable and believed to be unique. Other objects and features of the invention will be in part apparent and in part pointed out hereinafter.

In accordance with the invention, antibacterial fibers are produced by preparing a solution containing monovalent copper cations and a solution containing anions selected from the group consisting of carbonate, borate and mixtures thereof. The solution of monovalent copper cations and the solution of carbonate and borate anions may be provided as two baths or combined into a single bath. The fibers are immersed in the cation and anion solutions to permit adsorption of the cations and anions onto said fibers to increase the antibacterial properties of the fibers. The fibers are then removed from said cation and anion solutions.

The invention summarized above comprises the methods and products hereinafter described, the scope of the invention being indicated by the subjoined claims.

DETAILED DESCRIPTION OF THE INVENTION

According to the present invention, a copper compound containing carbonate, borate or mixture thereof is adsorbed on fibers. In a preferred embodiment, the fibers are preferably from the acrylic or modacrylic family, although other types of fibers, natural or synthetic or fiber blends, could be used. In another preferred embodiment, polyester or nylon fibers are graft polymerized with acrylonitrile and the graft polymer fibers treated in a manner such that a copper compound containing carbonate, borate or mixture thereof is adsorbed on the fibers. Modified graft polymerization techniques may be used to treat cotton, wool, linen and fiber blends. The fiber may be treated individually or in a collective form such as yarn, non-woven fabric, woven cloth or even as a manufactured item. If the fiber is treated individually, it may be transformed after treatment into a fiber mass by conventional methods and then sewed or otherwise formed into useful items.

To impart antibacterial properties, the fibers are preferably scoured prior to treatment to clean the surface of the fibers and then immersed in a bath containing a bivalent copper compound and a reducing agent or a solution containing a monovalent copper compound. The solution of copper ions is prepared by dissolving a copper salt such as copper sulfate, copper chloride, copper nitrate, copper acetate and other compounds which can liberate copper ions in water. Other solutions which contain copper ions such as copper acetate dissolved in alcohol or dissolved in mixtures of alcohol and water and so forth are suitable.

When the copper ions are not already in the monovalent state, a reducing agent capable of reducing the copper ions in solution to cuprous ions is added to the solution. Suitable reducing agents for this purpose include metallic copper, sodium formate, ferrous sulfate, sodium bisulfite, sodium hypophosphite, ammonium vanadate, hydroxylamine sulfate, furfural, glucose, hydroxylamine, sodium dithionite and so forth, including mixtures. Other known reducing agents such as hydrogen containing gas may be substituted or added if desired.

The bath with the solution of copper ions may contain an acid or a salt for adjusting the pH of the bath. Suitable acids for this purpose are inorganic acids such as sulfuric acid or nitric acid or organic acids such as acetic acid or citric acid. Suitable salts include ammonium sulfate.

The fibers are also immersed in a bath containing a solution of borate or carbonate anions or a mixture of borate and carbonate anions. The anion solution should not contain substantial quantities of anions which when adsorbed on the fibers affect the fibers capacity to sustain the antibacterial properties or dying compatibility imparted by this method. The anion containing solution can be prepared by dissolving a salt containing the anion in water or in some other suitable polar solvent or mixture of solvents. The borate anions may be obtained from a group of materials including, by way of example, sodium borate, sodium perborate, borax, sodium metaborate, sodium boroformate, potassium borate, lithium borate, lithium metaborate dihydrate, magnesium borate, calcium borate, magnesium borocitrate, boric acid, boric oxide and other compounds which can liberate borate anions and mixtures thereof. The carbonate anions may be obtained from a group of materials which includes sodium carbonate, sodium bicarbonate, sodium carbonate monohydrate, sodium carbonate peroxide, sodium percarbonate, sodium sesquicarbonate, potassium carbonate, potassium bicarbonate, potassium percarbonate, sodium potassium carbonate, lithium carbonate, lithium bicarbonate, rubidium carbonate, cesium carbonate and other compounds which can liberate carbonate anions and mixtures thereof. Other known means of introducing carbonate anions into solution such as sparging the solution with a carbon dioxide containing gas may be substituted or added if desired.

The method of treating fibers according to the present invention involves a one-bath or two-bath treatment. In the two-bath treatment, the fibers are first immersed in the solution of copper ions, then the copper impregnated fibers are washed with water and spun dry, then immersed in the solution containing the borate or carbonate ions. Alternatively, in the one-bath treatment, the fibers are immersed in a solution containing both the monovalent copper ions and the borate or carbonate ions. After immersion the treated fiber is usually washed with water, then spun dry and finally dried in a conventional dryer or in a microwave oven. The two bath method may permit more effective recovery, recycling and disposal of the ingredients utilized in the baths.

The temperature of the treatment bath is preferably within the range of 40° C. to 130° C. to efficiently adsorb the ions. At high treatment temperatures, the strength of the fibers may deteriorate although the time of immersion will be shorted. At lower temperatures, the time of treatment may be undesirably long.

After the fibers have been treated in the bath(s) it is normally dried and, if not already formed in a desired fiber mass, spun, knitted, woven, matted or the like and used to manufacture clothing, bed cloths and so forth. Fibers produced by this invention may be used in underwear, socks, surgery garments, bed sheets, carpets, masks, filters, pet beds and many other products where antibacterial properties are desirable.

The following examples illustrate the invention.

EXAMPLE 1

An acrylic fabric measuring 2.5 cm by 2.5 cm was thoroughly scoured and immersed in a heated bath containing 0.2 liter of water. The bath additionally contained a 170 $cm^2$ copper plate, 0.3 weight percent of copper sulfate, 0.3 weight percent of sodium carbonate and 0.1 weight percent of sulfuric acid. The amount of each compound in solution is relative to the water content. The fabric to solution weight ratio was 1:40. The bath containing the fabric was gradually heated to 90° C. and the fabric immersed for 60 minutes while the bath was held at 90° C. The fabric was then removed from the bath and washed with deionized water and allowed to dry. The fabric exhibited a pale pink color when viewed in natural light. Analysis of the dried treated fabric confirmed that 6.6 percent of its weight was copper carbonate based on the dry weight of the untreated fabric sample. The antibacterial properties are listed in Table 1.

EXAMPLE 2

An acrylic fabric measuring 2.5 cm by 2.5 cm was thoroughly scoured and immersed in a heated bath containing 0.2 liter of water, a 170 $cm^2$ copper plate, 1.0 weight percent of copper chloride and 0.15 weight percent of sulfuric acid. The amount of each compound in solution is relative to the water content. The fabric to solution weight ratio was 1:40. The bath containing the fabric was gradually heated to 90° C. and the fabric immersion continued for 40 minutes after the bath reached temperature. The fabric was removed and washed with deionized water and spun dry. The treated fabric was then immersed in a heated bath containing 1.0 weight percent relative to water of sodium carbonate. The fabric to solution weight ratio was 1:40 based on the dry weight of the original untreated sample. The bath was gradually heated to 90° C. and the fabric immersed for one hour at temperature. The fabric was removed from the bath and washed again with water, spun dry and then dried in a conventional oven. The fabric exhibited a pale yellowish color and tests confirmed that 5.6 percent of its weight was copper carbonate which had adsorbed onto the fibers based on the dry weight of the untreated fabric sample. The antibacterial properties are listed in Table 1.

EXAMPLE 3

A bath containing 0.3 weight percent of copper sulfate, 0.3 weight percent of sodium bisulfite, 0.3 weight percent of sodium carbonate and 0.1 weight percent of sulfuric acid was prepared. The amount of each compound in solution is relative to the water content. The fabric to solution weight ratio was 1:40. The fabric was immersed in the bath and the bath heated to 80° C. The fabric sample was removed from the solution 90 minutes after the solution reached treatment temperature. The fabric exhibited a pale pink color and tests confirmed that 6.2 weight percent of copper carbonate had adsorbed onto the fibers.

EXAMPLE 4

A first bath containing 1.0 weight percent of copper chloride, 1.0 weight percent of sodium bisulfite and 0.15 weight percent of sulfuric acid was prepared. The amount of each compound in solution is relative to the water content. The fabric to solution weight ratio was 1:40. The fabric was immersed in the bath which was held at 90° C. for one hour. The fabric was removed from the first bath, washed with water and then immersed in a second bath containing a solution which had 1.0 weight percent of sodium carbonate. The bath was heated to 90° C. and the fabric immersed for one hour at temperature. The fabric exhibited a pale yellowish color and tests confirmed that 5.3 weight percent of copper carbonate had been adsorbed.

EXAMPLE 5

A bath containing 0.3 weight percent of copper sulfate, 0.3 weight percent of hydroxylamine, 0.3 weight percent of sodium carbonate and 0.1 weight percent of sulfuric acid was prepared. The amount of each compound in solution is relative to the water content. The fabric to solution weight ratio was 1:40. The fabric was immersed in the bath which was heated gradually to 80° C. for 90 minutes. After treatment the fabric exhibited a pale pink color and tests confirmed that 6.8 weight percent of copper carbonate adsorbed.

EXAMPLE 6

An acrylic fabric measuring 2.5 cm by 2.5 cm was thoroughly scoured and immersed in a heated bath containing 0.2 liter of water. The bath additionally contained a 170 $cm^2$ copper plate, 0.5 weight percent of copper sulfate, 0.5 weight percent of sodium borate and 0.1 weight percent of sulfuric acid. The amount of each compound in solution is relative to the water content. The fabric to solution weight ratio was 1:40. The bath containing the fabric was gradually heated to 90° C. and the fabric immersed for 60 minutes. The fabric was then removed from the bath and washed with deionized water and allowed to dry. The fabric exhibited a pale orange color when viewed in natural light. Analysis of the fabric confirmed that 8.7 percent of its weight was copper borate.

EXAMPLE 7

An acrylic fabric measuring 2.5 cm by 2.5 cm was immersed in a heated first bath containing 0.2 liter of water, a 170 $cm^2$ copper plate, 1.0 weight percent of copper chloride and 0.15 weight percent of sulfuric acid. The amount of each compound in solution is relative to the water content. The fabric to solution weight ratio was 1:40. The bath containing the fabric was gradually heated to 80° C. and the fabric immersed for one hour. The treated fabric was then removed from the first bath, washed with water and then immersed in a heated second bath containing 1.0 weight percent relative to water of sodium borate. The second bath was heated to 90° C. and the fabric immersed for one hour. The fabric exhibited a pale orange color and tests confirmed that 7.6 percent of its weight was copper borate which had adsorbed onto the fibers.

EXAMPLE 8

A bath containing 0.5 weight percent of copper sulfate, 0.5 weight percent of sodium bisulfite, 0.5 weight percent of sodium borate and 0.1 weight percent of sulfuric acid was prepared. The amount of each ingredient in solution is relative to the water content. The fabric to solution weight ratio was 1:40. The fabric was immersed in the bath and the bath heated gradually to 90° C. After immersion at 90° C. for one hour the fabric sample was removed from the solution and then washed with water and dried. The fabric exhibited a pale orange color and tests confirmed that 8.2 weight percent of copper borate had adsorbed onto the fibers.

EXAMPLE 9

A first bath containing 1.0 weight percent of copper chloride, 1.0 weight percent of sodium bisulfite and 0.15 weight percent of sulfuric acid was prepared. The amount of each compound in solution is relative to the water content. The fabric to solution weight ratio was 1:40. The fabric was immersed in the bath which was heated to 90° C. for one hour. The fabric was removed from the first bath, washed with water and then spun dry and then immersed in a second bath containing a solution which had 1.0 weight percent of borax. The bath was heated gradually to 90° C. and the fabric immersed for one hour at temperature. The fabric exhibited a pale orange color and tests confirmed that 7.5 weight percent of copper borate had been adsorbed.

EXAMPLE 10

A bath containing 0.5 weight percent of copper sulfate, 0.5 weight percent of hydroxylamine, 0.5 weight percent of borax and 0.1 weight percent of sulfuric acid was prepared. The amount of each ingredient in solution is relative to the water content. The fabric to solution weight ration was 1:40. The fabric was immersed in the bath which was heated to 90° C. The fabric which was removed from the bath after one hour at temperature was washed with water. The fabric exhibited a pale orange color. Tests confirmed that 8.6 weight percent of copper borate had adsorbed onto the fibers.

The treated fabric from Example 10 was further treated by immersion in an aqueous solution containing 1 weight percent of Brilliant Red N-4G (cationic dye obtained from First Chemical Company, Ltd., Taipei, Taiwan) at 90° C. for 40 minutes. The treated fabric displayed red color. This dyed fabric from the borate system and the fabric from Example 5 in the carbonate system were subjected to a repeated washing test ten times according to JIS L 1405-A2. The antibacterial properties of these samples are listed in Table 1.

EXAMPLE 11

A group of polyester fibers were scoured and immersed in a heated bath which contained 0.2 liters of water, 3 weight percent of acrylonitrile, 1 weight percent of sodium stearate and 0.5 weight percent of potassium persulfate. The amount of each compound in solution is relative to the water content. The fiber to solution weight ratio was 1:40. The bath containing the fibers was gradually heated to 70° C. and the fibers immersed for 60 minutes after the bath reached temperature. The fibers were removed from the solution and washed with deionized water to remove unreacted residues. The treated fibers from the first bath were then immersed in a heated bath which contained 0.5 weight percent copper sulfate, 0.5 weight percent of hydroxylamine, 0.5 weight percent of borax, and 0.1 weight percent sulfuric acid. The fiber to solution ratio was 1:40. The bath was gradually heated to 100° C. and the fibers immersed for one hour. The fibers were removed from the second solution, washed with water and dried. The fibers had a pale orange color and tests confirmed that 7.5 weight percent of copper borate had been adsorbed.

EXAMPLE 12

Nylon fibers were scoured and immersed in a bath which contained 3 weight percent of acrylonitrile, 0.1 weight percent of ammonium persulfate and 0.25 weight percent of sodium bisulfite. The amount of each compound in solution is relative to the water content. The fiber to solution ratio was 1:40. The bath was gradually heated to 70° C. and the fibers were maintained in the bath for 60 minutes after the bath reached temperature. The fibers were then removed from the bath and washed with water to remove unreacted residues. The treated fibers were then immersed in a solution which contained 0.5 weight percent of copper sulfate, 0.5 weight percent hydroxylamine, 0.5 weight percent sodium borate, and 0.1 weight percent of sulfuric acid. The fiber to solution weight ratio was 1:40. The bath was heated gradually to 95° C. and the fibers were removed after one hour at temperature. The fibers were washed with water and dried. The fibers exhibited a pale orange color and test showed that 7.9 weight percent of copper borate has adsorbed onto the fiber.

ANTIBACTERIAL TEST METHODS

Method 1: *S. Aureus* (Staphylococcus Aureus) CCRC 12154 was activated twice on nutrient broth for 20 hours at 37° C. and 150 rpm for stock. The total count was made in 0.1 ml media after incubation.

Inoculate 0.1 ml of prepared stock of *S. aureus* into flasks with control and testing samples (a one inch square) separately; incubate the flasks at 37° C. and 150 rpm for 20 hours. 0.1 ml of suspension was smeared on the nutrient agar plate for the test of colony formation unit (C.F.U./ml) after incubation at 37° C. for 20 hours. The efficiency ratio was then calculated.

Method 2: *T. Rubrum* (Trichophyton Rubrum) was activated twice on mycological agar for 5–7 days at 25° C. and 150 rpm. The total count was tested in 0.1 ml media after incubation.

Inoculate 0.1 ml of prepared stock of T. Rubrum into flasks with control and testing samples (a one inch square) separately; incubate and shake the flasks at 25° C., 150 rpm for 20 hours; smear 0.1 ml of suspension on potato dextrose agar for the test of colony formation unit (C.F.U./ml) after incubation at 25° C. for 3–5 days; calculate the efficiency ratio.

Method 3: *T. Mentagrophytes* (Trichopyton Mentagrophytes) CCRC 32066 was activated twice on Sabouraud'sglucose agar for 5–7 days at 24° C. and 150 rpm. The total count was made in 0.1 ml media after incubation.

Inoculate 0.1 ml of prepared stock of T. Mentagrophytes into flasks with control and testing samples (a one inch square) separately; incubate the flasks at 24° C., 150 rpm for 20 hours; smear 0.1 ml of suspension on Sabouraud'sglucose agar for the test of colony formation unit (C.F.U./ml) after incubation at 24° C. for 3–5 days; calculate the efficiency ratio.

TABLE 1

| Sample Number* | Bacterial Type | Initial Count CFU/ml | Final Count CFU/ml | Control CFU/ml | Efficiency Ratio % |
|---|---|---|---|---|---|
| *Copper Carbonate System* | | | | | |
| 1 | S. Aureus | $1.2 \times 10^7$ | 0 | $6.5 \times 10^7$ | 100 |
|   | T. Rubrum | $1.7 \times 10^5$ | $2.2 \times 10^2$ | $3.5 \times 10^5$ | 99.9 |
|   | T. Mentagrophytes | $1.8 \times 10^3$ | $2.1 \times 10^1$ | $5.7 \times 10^3$ | 99.6 |
| 2 | S. Aureus | $1.2 \times 10^7$ | 0 | $6.5 \times 10^7$ | 100 |
|   | T. Rubrum | $1.7 \times 10^5$ | $7 \times 10^2$ | $3.5 \times 10^5$ | 99.8 |
|   | T. Mentagrophytes | $1.8 \times 10^3$ | $3.4 \times 10^1$ | $5.7 \times 10^3$ | 99.4 |
| 3 | S. Aureus | $1.2 \times 10^7$ | 0 | $6.5 \times 10^7$ | 100 |
|   | T. Rubrum | $1.7 \times 10^5$ | $2.6 \times 10^2$ | $3.5 \times 10^5$ | 99.9 |
|   | T. Mentagrophytes | $1.8 \times 10^3$ | $2.7 \times 10^1$ | $5.7 \times 10^3$ | 99.5 |
| 4 | S. Aureus | $1.2 \times 10^7$ | 0 | $6.5 \times 10^7$ | 100 |
|   | T. Rubrum | $1.7 \times 10^5$ | $1 \times 10^3$ | $3.5 \times 10^5$ | 99.7 |
|   | T. Mentagrophytes | $1.8 \times 10^3$ | $5.5 \times 10^1$ | $5.7 \times 10^3$ | 99.0 |
| 5 | S. Aureus | $1.2 \times 10^7$ | 0 | $6.5 \times 10^7$ | 100 |
|   | T. Rubrum | $1.7 \times 10^5$ | $8.5 \times 10^1$ | $3.5 \times 10^5$ | 100 |
|   | T. Mentagrophytes | $1.8 \times 10^3$ | $1 \times 10^1$ | $5.7 \times 10^3$ | 99.8 |
| *Copper Borate System* | | | | | |
| 6 | S. Aureus | $1.1 \times 10^7$ | 0 | $7.2 \times 10^7$ | 100 |
|   | T. Rubrum | $1.8 \times 10^5$ | 0 | $3.9 \times 10^5$ | 100 |
|   | T. Mentagrophytes | $1.6 \times 10^3$ | 0 | $5.4 \times 10^3$ | 100 |
| 7 | S. Aureus | $1.1 \times 10^7$ | 0 | $7.2 \times 10^7$ | 100 |
|   | T. Rubrum | $1.8 \times 10^5$ | $1 \times 10^2$ | $3.9 \times 10^5$ | 100 |
|   | T. Mentagrophytes | $1.6 \times 10^3$ | $1 \times 10^1$ | $5.4 \times 10^3$ | 99.8 |
| 8 | S. Aureus | $1.1 \times 10^7$ | 0 | $7.2 \times 10^7$ | 100 |
|   | T. Rubrum | $1.8 \times 10^5$ | 0 | $3.9 \times 10^5$ | 100 |
|   | T. Mentagrophytes | $1.6 \times 10^3$ | 0 | $5.4 \times 10^3$ | 100 |
| 9 | S. Aureus | $1.1 \times 10^7$ | 0 | $7.2 \times 10^7$ | 100 |
|   | T. Rubrum | $1.8 \times 10^5$ | $3 \times 10^2$ | $3.9 \times 10^5$ | 99.9 |
|   | T. Mentagrophytes | $1.6 \times 10^3$ | $2.5 \times 10^1$ | $5.4 \times 10^3$ | 99.5 |
| 10 | S. Aureus | $1.1 \times 10^7$ | 0 | $7.2 \times 10^7$ | 100 |
|    | T. Rubrum | $1.8 \times 10^5$ | 0 | $3.9 \times 10^5$ | 100 |
|    | T. Mentagrophytes | $1.6 \times 10^3$ | 0 | $5.4 \times 10^3$ | 100 |
| 11 | S. Aureus | $1.8 \times 10^7$ | 0 | $7.5 \times 10^7$ | 100 |
| 12 | S. Aureus | $1.8 \times 10^7$ | 0 | $7.5 \times 10^7$ | 100 |

*Sample Number: The Sample Numbers are for fabric treated according to the corresponding Example Numbers except the washed fabric from Example 5 was used for Sample 5 and the dyed and washed fabric from Example 10 was used for Sample 10.

TABLE 2

Tests of Fastness and Other Properties

| Property | Testing Result | | Test Method |
|---|---|---|---|
|  | Untreated Acrylic | Dyed and Washed Fabric from Example 10 |  |
| Breaking Strength (g) | 361.7 | 363.5 | ASTM D2256-88 option A1 |
| Color Fastness to Washing |  | 4.5 | AATCC61-1989 2A |
| Color Fastness to Perspiration |  | 4.5 | AATCC15-1989 |
| Color Fastness Crocking |  | 4.5 | AATCC8-1989 |
| Color Fastness Light |  | L4 | AATCC16-1990 option A |

In view of the above, it will be seen that the several objects of the invention are achieved and other advantageous results attained. As various changes could be made in the above methods and products without departing from the scope of the invention, it is intended that all matter contained in the above description shall be interpreted as illustrative and not in a limiting sense.

What is claimed is:

1. A method of treating fibers to render the fibers antibacterial, said method comprising the steps of:

a) preparing a solution containing monovalent copper cations;

b) immersing said fibers in said solution for a period of time sufficient for adsorption of said copper cations;

c) at the same time or subsequently, treating said fibers in a solution containing anions wherein said anions are selected from the group consisting of borate, carbonate and mixtures thereof for period of time sufficient for adsorption of said anions;

d) removing said copper containing fibers from the solution containing anions.

2. The method of treating fibers of claim 1 wherein the solution containing the copper cations is prepared in situ by reducing a solution of divalent copper cations with a reducing agent.

3. The method of treating fibers of claim 2 wherein the reducing agent is selected from the group consisting of metallic copper, sodium formate, ferrous sulfate, sodium bisulfite, sodium hypophosphite, ammonium vanadate, hydroxylamine sulfate, furfural, glucose, hydroxylamine, sodium dithionite, gases containing hydrogen and mixtures thereof.

4. The method of treating fibers of claim 1 wherein the solution containing the copper cations is an aqueous solution.

5. The method of treating fibers of claim 1 wherein the copper cations are selected from the group consisting of copper sulfate, copper chloride, copper nitrate, copper acetate and mixtures thereof.

6. The method of treating fibers of claim 1 wherein the borate anions are selected from the group consisting of sodium borate, sodium perborate, borax, sodium metaborate, sodium boroformate, potassium borate, lithium borate, lithium metaborate dihydrate, magnesium borate, calcium borate, magnesium borocitrate, boric acid, boric oxide and mixtures thereof and wherein the carbonate anions are selected from the group consisting of sodium carbonate, sodium bicarbonate, sodium carbonate monohydrate, sodium carbonate peroxide, sodium percarbonate, sodium sesquicarbonate, potassium carbonate, potassium bicarbonate, potassium percarbonate, sodium-potassium carbonate, lithium carbonate, lithium bicarbonate, rubidium carbonate, cesium carbonate, gases containing carbon dioxide and mixtures thereof.

7. The method of treating fibers of claim 1 wherein said fibers are sequentially:

a) immersed in the first solution containing monovalent copper cations and then removed from said first solution;

b) subsequently immersed in the second solution containing anions wherein said anions are selected from the group consisting of borate, carbonate and mixtures thereof;

c) removing said fibers from the solution containing anions.

8. The method of treating fibers of claim 1 wherein said fibers are sequentially:

a) immersed in a mixture of the solution containing monovalent copper cations and the solution containing anions wherein said anions are selected from the group consisting of borate, carbonate and mixtures thereof;

b) removing said fibers from the mixture of the solutions.

* * * * *